United States Patent [19]
Parikh et al.

[11] Patent Number: 5,922,355
[45] Date of Patent: Jul. 13, 1999

[54] COMPOSITION AND METHOD OF PREPARING MICROPARTICLES OF WATER-INSOLUBLE SUBSTANCES

[75] Inventors: Indu Parikh, Chapel Hill; Ulagaraj Selvaraj, Apex, both of N.C.

[73] Assignee: Research Triangle Pharmaceuticals, Durham, N.C.

[21] Appl. No.: 08/939,699

[22] Filed: Sep. 29, 1997

Related U.S. Application Data

[62] Division of application No. 08/701,483, Aug. 22, 1996.

[51] Int. Cl.$^6$ ........................................... A61K 9/14
[52] U.S. Cl. ..................... 424/489; 424/461; 424/464; 424/468; 424/450
[58] Field of Search .................. 424/427, 489, 424/428, 485, 450

[56] References Cited

U.S. PATENT DOCUMENTS

| | | |
|---|---|---|
| 4,411,933 | 10/1983 | Samejima et al. . |
| 4,963,367 | 10/1990 | Ecanow ................................... 424/450 |
| 5,091,187 | 2/1992 | Haynes . |
| 5,326,552 | 7/1994 | Na et al. . |
| 5,364,633 | 11/1994 | Hill et al. . |
| 5,389,377 | 2/1995 | Chagnon et al. ....................... 424/485 |
| 5,447,710 | 9/1995 | Na et al. . |

FOREIGN PATENT DOCUMENTS

| | | |
|---|---|---|
| 0391369 | 4/1990 | European Pat. Off. . |
| 0 601618 A2 | 6/1994 | European Pat. Off. . |
| 0 602 700 A2 | 6/1994 | European Pat. Off. . |
| WO 94/20072 | 9/1994 | WIPO . |
| WO 97/14407 | 4/1997 | WIPO . |

*Primary Examiner*—Thurman K. Page
*Assistant Examiner*—William E. Benston, Jr.
*Attorney, Agent, or Firm*—Nixon & Vanderhye

[57] ABSTRACT

Submicron size particles of pharmaceutical or other water-insoluble or poorly water-insoluble substances are prepared using a combination of one or more surface modifiers/surfactants such as polaxomers, poloxamines, polyoxyethylene sorbitan fatty acid esters and the like together with natural or synthetic phospholipids. Particles so produced have a volume weighted mean particle size at least one-half smaller than obtainable using a phospholipid alone. Compositions so prepared are resistant to particle size growth on storage.

11 Claims, No Drawings

COMPOSITION AND METHOD OF PREPARING MICROPARTICLES OF WATER-INSOLUBLE SUBSTANCES

This application is a division of application Ser. No. 08/701,483, filed Aug. 22, 1996.

This invention relates to compositions and procedures that yield sub-micron and micron stable particles of water-insoluble or poorly soluble drugs or other industrially useful insoluble compounds. The compositions of this invention include combinations of natural or synthetic phospholipds, and one or more non-ionic, anionic or cationic surfactants coated or adhered onto the surfaces of the water insoluble-compound particles. The combination of phospholipids and surfactants allows the formation and stabilization of the sub-micron and micron size compound particles via hydrophilic, lipophilic and electrostatic interactions and therefore prevent these particles from aggregation or flocculation.

BACKGROUND OF THE INVENTION

There is a critical need in the pharmaceutical and other biological based industries to formulate water-insoluble or poorly soluble substances into formulations for oral, injectable, inhalation and ophthalmic routes of delivery. Water insoluble compounds are those having poor solubility in water, that is <5 mg/ml at physiological pH (6.5–7.4). Preferably their water solubility is <1 mg/ml, more preferably <0.1 mg/ml. It is desirable that the drug is stable in water as a dispersion; otherwise a lyophilized or spray-dried solid form may be desirable.

As used herein, "micro" refers to a particle having diameter of from nanometers to micrometers. Microparticles, as used herein, refer to solid particles of irregular, non-spherical or spherical shapes. Formulations containing these microparticles provide some specific advantages over the unformulated non-micronized drug particles, which include improved oral bioavailability of drugs that are poorly absorbed from GI tract, development of injectable formulations that are currently available only in oral dosage form, less toxic injectable formulations that are currently prepared with organic solvents, sustained release of intramuscular injectable drugs that are currently administered through daily injection or constant infusion, and preparation of inhaled, ophthalmic formulation of drugs that otherwise could not be formulated for nasal or ocular use.

Current technology for delivering insoluble drugs as described in U.S. Pat. Nos. 5,091,188; 5,091,187 and 4,725,442 focuses on (a) either coating small drug particles with natural or synthetic phospholipds or (b) dissolving the drug in a suitable lipophilic carrier and forming an emulsion stabilized with natural or semisynthetic phospholipids. One of the disadvantages of these formulations is that certain drug particles in suspension tend to grow over time because of the dissolution and reprecipitation phenomenon known as the "Oswald ripening".

DESCRIPTION OF THE INVENTION

The present invention focuses on preparing submicron size particles using a combination of surface modifier(s) with a phospholipid, and how the growth of particle size, and hence storage stability, is controlled by adding a combination of surface modifier(s) with a phospholipid to the formulation.

The use of a surface modifier or combination of surface modifiers in addition to a phospholipid is characterized by its ability to result in volume weighted mean particle size values that are (i) at least 50% and preferably about 50–90% smaller than what can be achieved using phospholipid alone without the use of a surfactant with the same energy input, and (ii) provide compositions resistant to particle size growth on storage. While resistance to particle size growth on storage was an objective of this invention we were surprised to observe a significant reduction in particle size with the addition of the surfactant. In order to achieve the advantages of the present invention it is necessary that the phospholipid and the surfactant both be present at the time of particle size reduction or precipitation.

Although we do not wish to be bound by any particular theory, it appears that these surface modifiers generally, that is phospholipids and one or more surfactants, adsorb to the surfaces of drug particles, and (a) convert lipophilic to hydrophilic surfaces with increased steric hindrance/stability, and (b) possibly modify zeta potential of surfaces with more charge repulsion stabilization. The concentrations of surface modifiers used in the process described here are normally above their critical micelle concentrations (CMC) and hence facilitate the formation of sub-micron particles by stabilizing the particles.

Phospholipid and surface modifier(s) are adsorbed on to the surfaces of drug particles in sufficient quantity to retard drug particle growth, reduce drug average particle size from 5 to 100 $\mu$m to sub-micron and micron size particles by one or combination of methods known in the art, such as sonication, homogenization, milling, microfluidization, precipitation or recrystallization or precipitation from supercritical fluid, and maintain sub-micron and micron size particles on subsequent storage as suspension or solid dosage form.

The concentration of phospholipid or surface modifier in the suspension or solid dosage form can be present in the range of 0.1 to 50%, preferably 0.2 to 20%, and more preferably 0.5 to 10%.

The formulations prepared by this invention may be lyophilized into powders, which can be resuspended or filled into capsules or converted into granules or tablets with the addition of binders and other excipients known in the art of tablet making.

By industrially useful insoluble or poorly soluble compounds we include biologically useful compounds, imaging agents, pharmaceutically useful compounds and in particular drugs for human and veterinary medicine. Water insoluble compounds are those having a poor solubility in water, that is less than 5 mg/ml at a physiological pH of 6.5 to 7.4, although the water solubility may be less than 1 mg/ml and even less than 0.1 mg/ml.

Examples of some preferred water-insoluble drugs include immunosuppressive and immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antarrhythmics, antihypertensive agents, antineoplastic agents, hormones, and nutrients. A detailed description of these and other suitable drugs may be found in *Remington's Pharmaceutical Sciences*, 18th edition, 1990, Mack Publishing Co. Philadelphia, Pa.

The phospholipid may be any natural or synthetic phospholipid, for example phosphatidylcholine, phosphatidylethanolamine, phosphatidylserine, phosphatidylinositol, phosphatidylglycerol, phosphatidic acid, lysophospholipids, egg or soybean phospholipid or a combination thereof. The phospholipid may be salted or desalted, hydrogenated or partially hydrogenated or natural semisynthetic or synthetic.

Examples of some suitable second surface modifiers include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylarnmonium bromide, chitosans and lauryldimethylbenzylammonium chloride, (e) colloidal clays such as bentonite and veegum. A detailed description of these surfactants may be found in Remington's Pharmaceutical Sciences, and Theory and Practice of Industrial Pharmacy, Lachman et al, 1986.

More specifically, examples of suitable second surface modifiers include one or combination of the following: polaxomers, such as Pluronic™ F68, F108 and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylene-diamine available from BASF, Triton™ X-200, which is an alkyl aryl polyether sulfonate, available from Rohm and Haas. Tween 20, 40, 60 and 80, which are polyoxyethylene sorbitan fatty acid esters, available from ICI Speciality Chemicals, Carbowax™ 3550 and 934, which are polyethylene glycols available from Union Carbide, hydroxy propylmethylcellulose, dimyristoyl phosphatidylglycerol sodium salt, sodium dodecylsulfate, sodium deoxycholate, and cetyltrimethylammonium bromide.

It is thought that some of the functions of the second surface modifier(s) as it relates to this invention are suppressing the process of Oswald Ripening and therefore maintaining the particle size, increasing the storage stability, minimizing sedimentation, and decreasing the particle growth during lyophilization and reconstitution; adhere or coat firmly onto the surfaces of water-insoluble drug particles and therefore modify the interfaces between the particles and the liquid in the resulting formulations; increase the interface compatibility between water-insoluble drug particles and the liquid; and possibly to orient preferentially themselves with the hydrophilic portion sticking into the aqueous solution and the lipophilic portion strongly adsorbed at the water-insoluble drug particle surfaces Considerable variations as to the identities and types of phospholipid and especially the surface active agent or agents should be expected depending upon the drug or active agent selected as the surface properties of these small particles are different. The most advantageous surface active agent for the insoluble drug will be apparent following empirical tests to identify the surfactant or surfactant system/combination resulting in the requisite particle size and particle size stability on storage over time.

Various procedures can be used to produce these stable sub-micron and micron size particles including mixing the insoluble substance with phospholipid and precipitating from a dissolved mixture of the substance, phospholipid and surfactant using other surfactants followed by sonication, milling, homogenization, microfluidization, and antisolvent and solvent precipitation. Mannitol and other agents may be added to adjust the final formulation to isotonicity as well as a stabilizing aid during drying.

Unless otherwise specified, all parts and percentages reported herein are weight per unit volume (w/v), in which the volume in the denominator represents the total volume of the system. Diameters of dimensions are given in millimeters (mm=$10^{-3}$ meters), micrometers ($\mu$m=$10^{-6}$ meters), nanometers (nm=$10^{-9}$ meters) or Angstrom units (=0.1 nm). Volumes are given in liters (L), milliliters (mL=$10^{-3}$L) and microliters ($\mu$L=$10^{-6}$L). Dilutions are by volume. All temperatures are reported in degrees Celsius. The compositions of the invention can comprise, consist essentially of or consist of the materials set forth and the process or method can comprise, consist essentially of or consist of the steps set forth with such materials.

The following examples further explain and illustrate the invention:

EXAMPLE 1

Microparticle-cyclosporine, of an immunosuppressive drug, was prepared as follows. The composition and concentration of excipients of the microparticle cyclosporine formulation are listed below:

| | |
|---|---|
| Cyclosporine | 50 mg/ml |
| Egg Phosphatidylcholine | 100 mg/ml |
| Mannitol | 55 mg/ml |
| Tween 80 | 10 mg/ml |
| Distilled Water | qs to 100% |
| Total Volume | 20 ml |

Cyclosporine with an average particle size from 5–100 $\mu$m, and mannitol were purchased from Sigma, egg phosphatidylcholine was produced by Pfanstiehl, Tween 80 was purchased from ICI.

The above components were placed in a 30 ml beaker and pre-mixed with a hand-held biohomogenizer (Honeywell DR 4200 model GP) for 1–5 min. During homogenization, dilute NaOH was added to the pre-mix to adjust the pH from 3.1 to 7±0.5. The pre-mix was placed in a water jacketed vessel (50 ml capacity) through which thermostated water at 4° C. was circulated to control the temperature of the formulation. The pre-mix was subjected to high shear energy of a probe sonicator (Fisher, model 550 Sonic Dismembrator) with a 0.5 inch diameter probe. Sonic pulses of 10 seconds at 10-seconds intervals at a power setting of 5 were utilized. During sonication the temperature of the formulation was 18±2° C. The pH during sonication was adjusted to 7±0.5 with dilute NaOH. Total sonication time employed to prepare the microparticle cyclosporine was usually 10.5 hours or less. The microparticle-cyclosporine formulation was placed in 20 ml vials and stored at 4 and 25° C. for further stability studies.

Particle size distribution of the suspension was analyzed with a NICOMP model 370 Particle Size Analyzer. This instrument utilizes photon correlation spectroscopy for particle sizing in the submicron region. A small volume of the suspension was diluted with water and placed in the cell of the particle size analyzer. Particle size determination based on volume weighted and number weighted particle size determination of the suspension, represented as a Gaussian distribution by the NICOMP 370 software, yielded the mean particle size values, which are listed below in Table I.

TABLE I

Volume-and Number-weighted Particle Size
Stability of Microparticle-Cyclosponne

| | Storage Time | | | |
|---|---|---|---|---|
| | Storage at 4° C. Mean Particle Size (nm) | | Storage at 25° C. Mean Particle Size (mn) | |
| Days | Volume-Weighted | Number-Weighted | Volume-Weighted | Number-Weighted |
| 0 | 361 | 63 | 361 | 63 |
| 7 | 337 | 69 | 423 | 67 |
| 51 | 358 | 76 | 455 | 66 |

Approximately 20 $\mu$l of the freshly prepared suspension was placed on a clean slide, with a clean cover glass, and examined under an Olympus BH2 microscope with 1000× magnification. An eye-piece equipped with a graticule was used to estimate the particle size. Most of the particles in the suspension were 0.3–0.5 $\mu$m. Furthermore, microscopic examination of the suspension confirmed non-agglomerated or flocculated micron and sub-micron size drug particles exhibiting Brownian motion.

EXAMPLE 2

For purpose of comparison (not according to the invention) using only a phospholipid, microparticle-cyclosporine with lecithin alone (without the second surface modifier, Tween 80) was also prepared using the same procedure as Example 1. The suspension was stored in 20 ml glass vials for storage stability studies. The volume and number weighted mean particle size values of the suspension stored at 4 and 25° C. are listed below. The results in Table II illustrate that the presence of lecithin alone (without the presence of Tween 80) does not provide the particle size reduction and enhancement in storage stability as described in Example 1.

TABLE II

Volume-weighted Particle Size Stability of
Microparticle-Cyclosporine

| | Storage Time | | | |
|---|---|---|---|---|
| | Storage at 4° C. Mean Particle Size (nm) | | Storage at 25° C. Mean Particle Size (mn) | |
| Days | Volume-Weighted | Number-Weighted | Volume-Weighted | Number-Weighted |
| 0 | 704 | 91 | 704 | 91 |
| 1 | 1472 | 503 | 2230 | 755 |
| 6 | 1740 | 416 | 2290 | 874 |

EXAMPLE 3

For purpose of comparison (not according to the invention) using only a surface modifier, microparticle-cyclosporine with Tween 80 alone (without a phospholipid, egg phosphatidylcholine) was also prepared using the same procedure as Example 1. The suspension was stored in 20 ml glass vials. The results in Table III illustrate that the presence of Tween 80 alone (without the presence of phospholipid does not provide particle size reduction as in Example 1.

TABLE III

Volume- and Number-weighted Particle Size
Stability of Microparticle-Cyclosporine

| | Mean Particle Size (nm) | |
|---|---|---|
| Day | Volume-Weighted | Number-Weighted |
| 0 | 521 | 67 |

EXAMPLE 4

The following microparticle-Docosanol formulations were prepared by the process of the invention with Tween 80, Tween 20, egg phosphatidylcholine, and/or Phospholipon 90H as surface modifiers. Docosanol is available from Sigma. The formulations were prepared according to the procedures of Example 1. The compositions and concentration of excipients of the microparticle formulations are listed below:

| Microparticle-Docosanol (Example 4.1, comparative) | |
|---|---|
| Docosanol | 20 mg/ml |
| Egg Phosphatidylcholine | 50 mg/ml |
| Mannitol | 55 mg/ml |
| Distilled Water | qs to 100% |
| Total Volume | 20 ml |
| Microparticle-Docosanol (Example 4.2) | |
| Docosanol | 20 mg/ml |
| Egg Phosphatidylcholine | 50 mg/ml |
| Mannitol | 55 mg/ml |
| Tween 80 | 10 mg/ml |
| Distilled Water | qs to 100% |
| Total Volume | 20 ml |
| Microparticle-Docosanol (Example 4.3) | |
| Docosanol | 20 mg/ml |
| Egg Phosphatidylcholine | 50 mg/ml |
| Mannitol | 55 mg/ml |
| Tween 20 | 10 mg/ml |
| Distilled Water | qs to 100% |
| Total Volume | 20 ml |
| Microparticle-Docosanol (Example 4.4) | |
| Docosanol | 20 mg/ml |
| Phospholipon 90H | 30 mg/ml |
| Mannitol | 55 mg/ml |
| Tween 80 | 10 mg/ml |
| Distilled Water | qs to 100% |
| Total Volume | 20 ml |
| Microparticle-Docosanol (Example 4.5, Comparative) | |
| Docosanol | 20 mg/ml |
| Mannitol | 55 mg/ml |
| Tween 80 | 10 mg/ml |
| Distilled Water | qs to 100% |
| Total Volume | 20 ml |

The mean volume-and number-weighted particle size values of the suspension were 286 nm, and 98 nm, respectively.

The volume weighted mean particle size values of the above suspension stored at 4° C. are listed below in Table IV.

TABLE IV

Volume-weighted and Number Weighted
Particle Size Stability of
Microparticle-Docosanol Stored at 4° C.

| Days | Storage Time | | | |
|---|---|---|---|---|
| | Mean Particle Size (nm) | | Mean Particle Size (nm) | |
| | Volume-Weighted | Number-Weighted | Volume-Weighted | Number-Weighted |
| | (Example 4.1) | | (Example 4.2) | |
| 0 | 688 | — | 112 | 55 |
| 30 | ND | ND | 156 | 81 |
| | (Example 4.3) | | (Example 4.4) | |
| 0 | 129 | 61 | 90 | 35 |
| 30 | 184 | 99 | 127 | 39 |

ND = Not Determined

The above data illustrate the much smaller particles produced by the present invention with the presence of a surfactant in addition to the phospholipid and that these particles retain their particle size over time without significant increase in size.

EXAMPLE 5

The following seven microparticle-RTP-4055 (an antiviral drug) formulations were prepared with combinations of Tween 80, Tetronic 908, Pluronic F-68, egg phosphatidylcholine, and/or phospholipon 90H as surface modifiers. The details of the sonication method are similar to those discussed in Example 1. The compositions and concentration of excipients of the microparticle formulations are listed below:

| Microparticle-RTP-4055 (Example 5.1, Comparative) | |
|---|---|
| RTP-4055 | 50 mg/ml |
| Egg Phosphatidylcholine | 50 mg/ml |
| Distilled Water | qs to 100% |
| Total Volume | 25 ml |

The mean volume weighted particle size of the suspension was 3195 nm.

| Microparticle-RTP-4055 (Example 5.2) | |
|---|---|
| RTP-4055 | 50 mg/ml |
| Egg Phosphatidylcholine | 50 mg/ml |
| Mannitol | 55 mg/ml |
| Pluronic F-68 | 5 mg/ml |
| Distilled Water | qs to 100% |
| Total Volume | 25 ml |

The mean volume- and number-weighted particle size values of the suspension were 672 nm and 76 nm respectively.

| Microparticle-RTP4055 (Example 5.3) | |
|---|---|
| RTP-4055 | 50 mg/ml |
| Egg Phosphatidylcholine | 50 mg/ml |
| Mannitol | 55 mg/ml |
| Tetronic 908 | 5 mg/ml |
| Distilled Water | qs to 100% |
| Total Volume | 25 ml |

The mean volume- and number- weighted particle size values of the suspension were 436 mn and 59 nm respectively.

| Microparticle-RTP-4055 (Example 5.4, Comparative) | |
|---|---|
| RTP-4055 | 50 mg/ml |
| Phospholipon 90H | 30 mg/ml |
| Distilled Water | qs to 100% |
| Total Volume | 25 ml |

The mean volume- number- weighted particle size values of the suspension were 1117 nm. and 108 nm respectively.

| Microparticle-RTP-4055 (Example 5.5) | |
|---|---|
| RTP-4055 | 50 mg/ml |
| Phospholipon 90H | 30 mg/ml |
| Mannitol | 55 mg/ml |
| Dimyristoylphosphatidyl choline (DMPG) | 3 mg/ml |
| Tween 80 | 10 mg/ml |
| Distilled Water | qs to 100% |
| Total Volume | 25 ml |

The mean volume weighted particle size of the suspension was 236 nm. The particle size of the suspension stored at 4° C. for 1 week and 1 month are 328 and 397 nm, respectively, which indicates the stability of the suspension.

| Microparticle-RTP-4055 (Example 5.6) | |
|---|---|
| RTP-4055 | 50 mg/ml |
| Phospholipon 90H | 30 mg/ml |
| Mannitol | 55 mg/ml |
| Tween 80 | 10 mg/ml |
| Distilled Water | qs to 100% |
| Total Volume | 25 ml |

The mean volume- and number- weighted particle size values of the suspension were 382 nm and 59 nm respectively. Within the error limits, there was no variation in the mean particle size after one week of storage at 4° C.

| Microparticle-RTP-4055 (Example 5.7, Comparative) | |
|---|---|
| RTP-4055 | 50 mg/ml |
| Mannitol | 55 mg/ml |
| Tween 80 | 10 mg/ml |
| Distilled Water | qs to 100% |
| Total Volume | 25 ml |

The volume- and number-weighted mean particle size values of the suspension were 545 nm, and 75 nm, respectively within the error limits, there was no variation in the mean particle size after one week of storage at 4° C.

EXAMPLE 6

The following six microparticle-Piroxicam formulations were prepared with combination of Tween 80, Tetronic 908, Pluronic F-68, and/or egg phosphatidylcholine as surface modifiers. Piroxicam was received from Cipla. The details of the sonication method are similar to those discussed in example 1. The compositions and concentration of excipients of the microparticle formulations are listed below:

| Microparticle-Piroxicam (Example 6.1) | |
|---|---|
| Piroxicam | 67 mg/ml |
| Egg Phosphatidylcholine | 67 mg/ml |
| Mannitol | 67 mg/ml |
| Tween 80 | 5 mg/ml |
| Tetronic 908 | 5 mg/ml |
| Distilled Water | qs to 100% (w/v) |
| Total Volume | 15 ml |

The mean volume- and number- weighted particle size values of the suspension were 674 nm and 72 nm respectively.

| Microparticle-Piroxicam (Example 6.2) | |
|---|---|
| Piroxicam | 67 mg/ml |
| Egg Phosphatidylcholine | 67 mg/ml |
| Mannitol | 67 mg/ml |
| Tetronic 908 | 5 mg/ml |
| Distilled Water | qs to 100% (w/v) |
| Total Volume | 15 ml |

The mean volume- and number- weighted particle size values of the suspension were 455 nm and 58 nm respectively.

| Microparticle-Piroxicam (Example 6.3) | |
|---|---|
| Piroxicam | 67 mg/ml |
| Egg Phosphatidylcholine | 67 mg/ml |
| Mannitol | 67 mg/ml |
| Pluronic F-68 | 5 mg/ml |
| Distilled Water | qs to 100% (w/v) |
| Total Volume | 15 ml |

The mean volume- and number- weighted particle size values of the suspension were 564 nm and 68 nm respectively.

| Microparticle-Piroxicam (Example 6.4) | |
|---|---|
| Piroxicam | 67 mg/ml |
| Egg Phosphatidylcholine | 67 mg/ml |
| Mannitol | 67 mg/ml |
| Tween 80 | 5 mg/ml |
| Cetyltrimethylammonium bromide | 10 mg/ml |
| Distilled Water | qs to 100% (w/v) |
| Total Volume | 15 ml |

The mean volume- and number- weighted particle size values of the suspension were 479 nm and 80 nm respectively.

| Microparticle-Piroxicam (Example 6.5) | |
|---|---|
| Piroxicam | 67 mg/ml |
| Egg Phosphatidylcholine | 67 mg/ml |
| Mannitol | 67 mg/ml |
| Cetyltrimethylammonium bromide | 10 mg/ml |
| Distilled Water | qs to 100% (w/v) |
| Total Volume | 15 ml |

The mean volume- and number- weighted particle size values of the suspension were 670 nm and 128 nm respectively.

| Microparticle-Piroxicam (Example 6.6, Comparative) | |
|---|---|
| Piroxicam | 67 mg/ml |
| Mannitol | 67 mg/ml |
| Tween 80 | 5 mg/ml |
| Tetronic 908 | 5 mg/ml |
| Distilled Water | qs to 100% |
| Total Volume | 25 ml |

The volume- and number- weighted particle size values of the suspension were 1184 nm and 385 nm, respectively.

What is claimed is:

1. In a process of preparing microparticles of a water-insoluble or poorly soluble compound comprising reducing the particle size by sonication, homogenization, milling, microfluidization and precipitation, or recrystallization and precipitation of the compound using antisolvent and solvent precipitation the improvement comprising the steps of:
   (1) prior to or during particle size reduction, mixing the particles of a water-insoluble or poorly soluble compound with (a) a natural or synthetic phospholipid and (b) at least one non-ionic, anionic or cationic surfactant, and thereafter
   (2) applying energy to the mixture sufficient to produce volume-weighted mean particle size values of said compound about 50% smaller than particles produced without the presence of the surfactant using the same energy input.

2. A process of stabilizing microparticles of a water-insoluble or poorly soluble compound and preventing particles from aggregating or flocculating by coating or adhering onto the surfaces of the water-insoluble or poorly soluble particles a mixture of a phospholipid together with at least one non-ionic, anionic or cationic surfactant, the process comprising the steps of:
   (1) mixing particles of a water-insoluble or poorly soluble compound with a phospholipid and at least one non-ionic, anionic or cationic surfactant, and thereafter
   (2) applying energy to the mixture sufficient to produce volume-weighted mean particle size values of said compound about 50% smaller than particles produced without the presence of the surfactant using the same energy input.

3. The process of claim 2 or wherein the phospholipid is of egg or plant origin or semisynthetic or synthetic in partly or fully hydrogenated form or in a desalted or salt form such as phosphatidylcholine, phospholipon 90H or dimyristoyl phosphatidylglyerol sodium, salt, phosphatidylethanolamine, phosphatidiylserine, phosphatidic acid, lysophospholipids, or combinations thereof.

4. The process of claim 1 or 2 wherein the surfactant is a polyoxyethylene sorbitan fatty acid ester, a block copolymer of ethylene oxide and propylene oxide, a tetrafunctional block copolymer derived from sequential addition of ethylene oxide and propylene oxide to ethylenediamine, an alkyl aryl polyether sulfonate, polyethylene glycol, hydroxy propylmethylcellulose, sodium dodecylsulfate, sodium deoxycholate, cetyltrimethylammonium bromide or combinations thereof.

5. The process of claim 1 or 2 wherein the surfactant is present above the critical micelle concentration.

6. The process of claim 1 or 2 in which the compound is a biologically useful compound or an imaging agent.

7. A composition comprising microparticles prepared by the process of claim 1.

8. A composition comprising microparticles produced by the process of claim 2.

9. The process of claim 1 or 2 wherein said compound has a solubility in water at pH 6.5 to 7.4 less than 5 mg/ml.

10. The process according to claim 9 wherein said compound has a solubility in water at pH 6.5 to 7.4 of less than 1 mg/ml.

11. The process according to claim 10 wherein said compound has a solubility in water at pH 6.5 to 7.4 of less than 0.1 mg/ml.

* * * * *